US007087735B2

(12) United States Patent
Gold

(10) Patent No.: US 7,087,735 B2
(45) Date of Patent: *Aug. 8, 2006

(54) BIVALENT BINDING MOLECULES OF 7 TRANSMEMBRANE G PROTEIN-COUPLED RECEPTORS

(75) Inventor: Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/729,667

(22) Filed: Dec. 5, 2003

(65) Prior Publication Data

US 2004/0091931 A1    May 13, 2004

Related U.S. Application Data

(60) Division of application No. 09/118,525, filed on Jul. 17, 1998, now Pat. No. 6,682,886, which is a continuation-in-part of application No. 08/956,699, filed on Oct. 23, 1997, now Pat. No. 6,083,696, which is a continuation of application No. 08/234,997, filed on Apr. 28, 1994, now Pat. No. 5,683,867.

(51) Int. Cl.
C07H 21/04 (2006.01)
C07H 21/02 (2006.01)

(52) U.S. Cl. .................. 536/23.1; 536/25.4; 435/7; 435/6; 435/4; 435/DIG. 15; 435/DIG. 16; 435/DIG. 17

(58) Field of Classification Search ............ 435/7, 435/6, 4, DIG. 15, 16, 17; 530/300; 536/23.1, 536/25.4
See application file for complete search history.

(56) References Cited

U.S. PATENT DOCUMENTS

| 5,270,163 A | 12/1993 | Gold et al. .............. 435/6 |
| 5,580,737 A | 12/1996 | Polisky et al. |
| 5,637,459 A | 6/1997 | Burke et al. ............ 435/6 |
| 5,648,214 A | 7/1997 | Nieuwlandt et al. ....... 435/6 |
| 5,656,739 A | 8/1997 | Cubicciotti ........... 536/23.1 |
| 5,683,867 A | 11/1997 | Biesecker et al. ......... 435/6 |
| 5,780,449 A | 7/1998 | Bracht et al. .......... 514/44 |

FOREIGN PATENT DOCUMENTS

| GB | 2 183 661 A | 6/1987 |
| WO | WO89/06694 | 7/1989 |
| WO | WO92/14843 | 9/1992 |
| WO | WO96/34879 | 11/1996 |
| WO | WO98/03632 | 1/1998 |

OTHER PUBLICATIONS

Carrithers and Lerner (1996) Chem. & Biol. 3:537.
Ellington & Szostak (1990) Abstract of papers presented at the 1990 meeting on RNA Processing, Cold Spring Harbor Laboratory, Cold Springs Harbor, NY, p. 84.
Fong et al. (1992) J. of Biol. Chem. 267:25664.
Joyce (1989) Gene 82:83.
Joyce & Inoue (1989) Nucleic Acid Research 17:711.
Kinzler & Vogelstein (1989) Nucleic Acids Research 17:3645.
Kramer et al (1974) J. Mol. 89:719.
Levisohn & Spiegelman (1969) PNAS USA 63:805.
Levisohn & Spiegelman (1968) PNAS USA 60:866.
Neri et al. (1995) J. Mol. Biol. 246:367.
Oliphant et al. (1989) Mol. Cell. Biol. 9:2944.
Oliphant & Struhl (1988) Nucleic Acid Research 16:7673.
Oliphant & Struhl (1987) Methods in Enzymology 155:568.
Oliphant et al. (1986) Gene 44:177.
Robertson & Joyce (1990) Nature 344:467.
Szostak, "Structure and Activity of Ribozymes," in *Redesigning the Molecules of Life*, (S.A. Benner ed.) Springer-Verlag Berlin Heidelberg, pp. 87-113, (1988).
Thiesen & Bach (1990) Nucleic Acid Research 18:3203.
Xu (1996) Proc. Natl. Acad. Sci. USA 93:7475-7480.

*Primary Examiner*—T. D. Wessendorf
(74) *Attorney, Agent, or Firm*—Swanson & Bratschun, L.L.C.

(57) ABSTRACT

Described herein are methods for identifying and preparing bivalent binding molecules to 7 transmembrane G protein-coupled receptors. The methods disclosed herein are based on the SELEX method for generating high affinity nucleic acid ligands. SELEX is an acronym for Systematic Evolution of Ligands by EXponential enrichment. The methods of this invention combine two or more binding domains to two or more different epitopes of the same 7 transmembrane G protein-coupled receptor. These bivalent binding molecules are useful as therapeutic and diagnostic agents.

5 Claims, 1 Drawing Sheet

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

His Asn Glu Trp Tyr Tyr Gly Leu Phe Tyr Cys Lys Phe
  1               5                  10

<210> SEQ ID NO 2
<211> LENGTH: 26
<212> TYPE: PRT
<213> ORGANISM: Homo sapiens

<400> SEQUENCE: 2

Thr Thr Glu Thr Met Pro Ser Arg Val Val Cys Met Ile Glu Trp Pro
  1               5                  10                  15

Glu His Pro Asn Lys Ile Tyr Glu Lys Val
              20                  25
```

BIVALENT BINDING MOLECULES OF 7 TRANSMEMBRANE G PROTEIN-COUPLED RECEPTORS

RELATEDNESS OF THE APPLICATION

The subject application is a divisional application of U.S. Ser. No. 09/118,525, filed Jul. 17, 1998; now U.S. Pat. No. 6,682,886, which is a continuation-in-part of U.S. Ser. No. 08/956,699, filed Oct. 23, 1997, now U.S. Pat. No. 6,083,696; which is a continuation of U.S. Ser. No. 08/234,997, filed Apr. 28, 1994, now U.S. Pat. No. 5,683,867; each of which are hereby incorporated in their entirety by reference.

FIELD OF THE INVENTION

Described herein are bivalent binding molecules that can activate or inhibit 7 transmembrane G protein-coupled receptors. Also described herein are methods for identifying and preparing bivalent binding molecules to 7 transmembrane G protein-coupled receptors. The methods disclosed herein are based on the SELEX method for generating high affinity nucleic acid ligands, also termed aptamers. SELEX is an acronym for Systematic Evolution of Ligands by EXponential enrichment. The bivalent binding molecules of this invention comprise two or more binding domains to two or more different epitopes of the same 7 transmembrane G protein-coupled receptor. In a preferred embodiment, at least one binding domain is an aptamer. These bivalent binding molecules are useful as therapeutic and diagnostic agents.

BACKGROUND OF THE INVENTION

The seven transmembrane receptors (also known as G protein-coupled receptors or 7TM G protein-coupled receptors) comprise a superfamily of structurally related integral proteins. 7TM G protein-coupled receptors exhibit detectable amino acid sequence similarity and all appear to share a number of structural features (See, FIG. 1). These features include: an extracellular amino terminus (EAT); seven predominantly hydrophobic alpha-helical domains (of about 20–30 amino acids) which are believed to span the cell membranes and are referred to as transmembrane domains (TMD1–7); six loops which connect the transmembrane domains (three extracellular loops (ELs) and three intracellular loops (ILs)); and a cytoplasmic carboxy terminus (CCT).

Each 7TM G protein-coupled receptor is predicted to associate with a particular heterotrimeric G protein (composed of α, β and γ subunits) at the intracellular surface of the plasma membrane. Upon binding of an agonist to the receptor, a conformational change occurs in the receptor, which enables interaction of the intracellular loops of the receptor with its associated intracellular, membrane-anchored heterotrimeric G protein. This causes the alpha-subunit of the G protein to exchange a bound GDP molecule for a GTP molecule and to dissociate from the β and γ subunits. The GTP-bound form of the alpha-subunit in turn stimulates specific intracellular signal-transducing enzymes and channels.

It has been proposed that 7TM G protein-coupled receptors adopt two major conformations: an active, G protein-coupled and thus transducing conformation and an inactive (non-transducing) conformation (Schwartz, T. W. et al., Cur. Pharmaceut. Design, 1:325–342 (1995)). The binding of an agonist or antagonist selectively stabilizes the active and the inactive receptor conformations, respectively, as predicted by the allosteric regulation of proteins as suggested by Monod, Wymann and Changeux (J. Mol. Biol., 263:7439–7442 (1965)). Agonists are thus extracellularly acting allosteric ligands that increase the signal transduction rate at intracellular sites upon binding. Antagonists are extracellularly acting ligands that inhibit signal transduction upon binding.

The 7TM G protein-coupled receptors are the largest family of cell-surface receptors comprising several hundred distinct receptors, and over 100 receptors have been cloned. The transmembrane segments of 7TM G protein-coupled receptor family members exhibit considerable homology, whereas the extracellular connecting loops are less conserved, showing high homology only between closely related receptor subtypes. The 7TM G protein-coupled receptors can be grouped based on their homology levels and/or the nature of the ligands they recognize. For example, the interleukin-8 receptor, the angiotensin II receptor, the thrombin receptor, the endothelin receptors, the N-formyl peptide receptor and the C5a receptor all bind peptide ligands and share 20–40% amino acid similarity.

The 7TM G protein-coupled receptors bind a wide variety of ligands of different molecular size ranging from small monoamines and other small molecules, to large neurotransmitters and peptide hormones. The family of 7TM G protein-coupled receptors also includes the receptors for light (rhodopsin), for odors (olfactory receptors) and for taste (gustatory receptors). Additionally, the conserved structure among 7TM G protein-coupled receptors has allowed for the cloning of many novel genes encoding 7TM G protein-coupled receptors whose natural ligand and function are yet to be elucidated. These receptors are referred to as "orphan" receptors. Table 1 lists a number of 7TM G protein-coupled receptors which have been cloned and expressed.

Because of the involvement of 7TM G-protein-coupled receptors in the regulation of many critically important biological functions and disease conditions, many of these functions and conditions may be influenced or determined by the state of activation or inhibition (e.g., blockade) of a 7TM G protein-coupled receptor. However, these receptors are difficult to purify. The proteins can be removed from the membrane only by the action of detergents, which denatures some proteins. In addition, most membrane proteins are not soluble in water. To date, few novel agonists or antagonists to these receptors have been identified. Common methods have involved generating antibodies to 7TM G protein-coupled receptors expressed in cells which have been administered to a host. Lerner et al. (PCT application No. WO 98/03632) have described peptide dimer agonists for 7TM G protein-coupled receptors. These dimers were comprised of two known peptide agonists or antagonists (e.g., natural ligands) to different 7TM G protein-coupled receptors.

It would be useful to be able to develop agonists and antagonists to the specific binding portions of 7TM G protein-coupled receptors. Attempts to achieve expression of only the ligand binding portion of a 7TM G protein-coupled receptor have been unreproducible or have resulted in inefficient and/or unpredictable levels of expression (Xie, U. B., et al, J. Biol. Chem. 265:21441–21420 (1990); Tsai-Morris, C. H., et al. J. Biol. Chem. 265:19385–19388 (1990)).

As suggested in Lerner et al., bivalent binding molecules can have utility as therapeutics. More specifically, bivalent and bispecific antibodies have many practical applications, including in immunodiagnosis and therapy. Bivalency can allow antibodies to bind to multimeric antigens with great avidity; multivalency theoretically can increase apparent binding affinity by several orders of magnitude (Crothers, D. M. et al., *Immunochemistry* 9: 341–351 (1972)). Bispecificity can allow the cross-linking of two antigens, for example, in recruiting cytotoxic T cells to mediate killing of a tumor cell. Specific examples of bivalent molecules capable of binding to adjacent epitopes include small bivalent antibodies composed of either antibody fragments ($F_{ab}$) or single chain antibodies ($F_v$) (Pack, P. et al., *Biochemistry* 31, 1579–1584 (1992); Holliger, P. et al., *Proc. Natl. Acad. Sci. USA* 90, 6444–6448 (1993); Mallender, W. D. et al., *J. Biol. Chem.*, 269: 199–206 (1994)). Neri, D. et al. (*J. Mol. Biol.*, 246:367–373 (1995)) developed a bispecific antibody fragment, binding two antibodies with a polypeptide chain, that recognizes adjacent and non-overlapping epitopes of lysozyme and is able to bind both epitopes simultaneously.

Bivalent peptides, such as receptor-adhesive modular proteins ("RAMPs"), have been used in an alternative approach to cell targeting. M. Engel et al., (*Biochemistry* 30: 3161–3169 (1991)) and C. A. Slate et al., (*Int. J. Peptide Protein Res.* 45: 290–298 (1995)) have designed large synthetic peptides, which contain two ligand sites separated by a spacer region and a dimerization domain.

The SELEX Process

A method for the in vitro evolution of nucleic acid molecules with highly specific binding to target molecules has been developed. This method, Systematic Evolution of Ligands by EXponential Enrichment, termed the SELEX process, is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Nucleic Acid Ligands," now U.S. Pat. No. 5,270,163 (see also WO 91/19813), each of which is herein specifically incorporated by reference. These applications, collectively referred to herein as the SELEX patent applications, describe a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", abandoned in favor of U.S. Ser. No. 08/198,670, now U.S. Pat. No. 5,707,796, describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands", abandoned in favor of U.S. Ser. No. 08/443,959, filed May 18, 1995, which was abandoned in favor of U.S. Ser. No. 08/612,895, filed Sep. 16, 1994, now U.S. Pat. No. 5,763,177, describes a SELEX-based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", now U.S. Pat. No. 5,580,737, describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX", abandoned in favor of U.S. Ser. No. 08/461,069, filed Jun. 5, 1995, now U.S. Pat. No. 5,567,588, and U.S. patent application Ser. No. 08/792,075, filed Jan. 31, 1997, entitled "Flow Cell SELEX", now U.S. Pat. No. 5,861,254, describe SELEX-based methods which achieve highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev", now U.S. Pat. No. 5,496,938, describes methods for obtaining improved nucleic acid ligands after the SELEX process has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337, describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", abandoned in favor of U.S. Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, now U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", now U.S. Pat. No. 5,756,703, describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459 and U.S. patent application Ser. No. 08/234,997, filed Apr. 28, 1994, entitled "Systematic Evolution of Ligands by Exponential Enrichment: Blended SELEX", now U.S. Pat. No. 5,683,867, respectively. The SELEX method further encompasses combining selected nucleic acid ligands with lipophilic or Non-Immunogenic, High Molecular Weight compounds in a diagnostic or therapeutic complex as described in U.S. patent application Ser. No. 08/434,465, filed May 4, 1995, entitled "Nucleic Acid Ligand Complexes", now U.S. Pat. No. 6,011,020. VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes", now U.S. Pat. No. 5,859,228. VEGF Nucleic Acid Ligands that are associated with a Lipophilic Compound, such as a glycerol lipid, or a Non-Immunogenic, High Molecular Weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes". VEGF Nucleic Acid Ligands that are associated with a non-immunogenic, high molecular weight compound or lipophilic compound are also further described in PCT application Publication No. WO 98/18480, filed Oct. 17, 1997, entitled "Vascular Endothelial Growth Factor (VEGF) Nucleic Acid Ligand Complexes". These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

The identification of nucleic acid ligands to small, flexible peptides via the SELEX method has been explored. Small peptides have flexible structures and usually exist in solution as an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214, filed Sep. 9, 1994, entitled "High-Affinity Oligonucleotide Ligands to the Tachykinin Substance P", which is incorporated herein by reference. In this patent, high affinity RNA nucleic acid ligands to substance P, an 11 amino acid peptide were identified.

Xu and Ellington (*Proc. Natl. Acad. Sci. USA*, 93:7475–7480 (1996)) employed the human immunodeficiency virus type 1 (HIV-1) Rev to further explore how peptide and protein epitopes are recognized by nucleic acid ligands. In this study, RNA nucleic acid ligands were selected to bind to the isolated $Rev_{34-50}$ peptide. It was observed that RNA nucleic acid ligands could not only recognize the sequence of this peptide, but that these nucleic acid ligands could also bind the corresponding native epitope on the Rev protein, albeit with lower affinity.

The present invention provides bivalent binding molecules comprising two or more binding domains which bind simultaneously to two or more epitopes of the same 7TM G protein-coupled receptor and thus increase the binding affinity relative to the binding of a single binding domain. The binding domains are identified using synthetic peptides corresponding to all or a portion of the extracellular binding domains and therefore purified and isolated receptor proteins are not required.

BRIEF SUMMARY OF THE INVENTION

The present invention describes bivalent binding molecules having binding affinity for two or more epitopes of the same 7TM G protein-coupled receptor and methods for generating and producing such bivalent binding molecules. The bivalent binding molecules described herein may be agonists, antagonists or superagonists. In one embodiment the bivalent binding molecules of the invention comprise a first binding domain coupled to a second binding domain, the first and second binding domains being ligands to a first and second epitopes. In preferred embodiments, the first and second epitopes are located on different extracellular loops of the same 7TM G protein-coupled receptor. In a preferred embodiment, at least one binding domain of the bivalent binding molecule is an aptamer. In one embodiment, the first and second binding domains are coupled via a linker.

In a preferred embodiment, both the first and second binding domains are aptamers to first and second epitopes of two different extracellular loops. In this embodiment, the aptamers are coupled to each other at either their 5' or 3' ends. In a preferred embodiment, the aptamers are SELEX-derived aptamers.

In another embodiment, the first binding domain is an aptamer to a first epitope of a 7TM G protein-coupled receptor, and the second binding domain is a non-aptamer binding domain that binds to a second epitope of the same 7TM G protein-coupled receptor.

In one embodiment of the method of this invention, a method for identifying bivalent binding molecules to 7TM G protein-coupled receptors is described, wherein the bivalent binding molecules comprise two binding domains, each of which is an aptamer. In this method, the bivalent binding molecules are identified generally by applying the Chimeric SELEX methods described in U.S. Pat. No. 5,637,459, filed Aug. 2, 1994, entitled "Systematic Evolution of Ligands by Exponential Enrichment: Chimeric SELEX", which is incorporated herein by reference.

In another embodiment of the method of this invention, a method for identifying bivalent binding molecules to 7TM G protein-coupled receptors is described, wherein one binding domain of the bivalent molecule is an aptamer and the other is a non-aptamer binding domain. In this method, the bivalent compounds are identified generally by applying the Blended SELEX methods described in U.S. Pat. No. 5,683,867, filed Apr. 28, 1994, entitled "Systematic Evolution of Ligands by Exponential Enrichment: Blended SELEX", which is incorporated herein by reference. Suitable non-aptamer binding domains include all or a portion of a natural ligand to the 7TM G protein-coupled receptor.

In another embodiment of the method of this invention, a method for identifying bivalent binding molecules to 7TM G protein-coupled receptors is described, wherein both binding domains are unnatural L-aptamers (mirror images of the natural D-aptamers). In other embodiments, the first binding domain is an aptamer of non-natural handedness to a first epitope and the second binding domain is either an aptamer of natural handedness or a non-aptamer binding domain to a second epitope.

This invention further includes the bivalent binding molecules to 7TM G protein-coupled receptors generated by the methods of this invention. These bivalent binding molecules may contain one or more modified nucleotides such as nucleotides modified at the 2'- and/or 5 and/or 8 positions. Such modifications include but are not limited to nucleotides containing 2'-amino (2'-$NH_2$), 2'-fluoro (2'-F) and 2'-O-methyl (2'-O-Me groups.

With certain 7TM G protein-coupled receptors, it may not be necessary for a binding ligand to be bivalent. Therefore this invention further includes aptamers to 7TM G protein-coupled receptors identified by the SELEX process which can act as agonists or antagonists of the receptor.

This invention further provides a method for treating diseases or conditions mediated by 7TM G protein-coupled receptors.

DETAILED DESCRIPTION OF THE INVENTION

Figure 1:
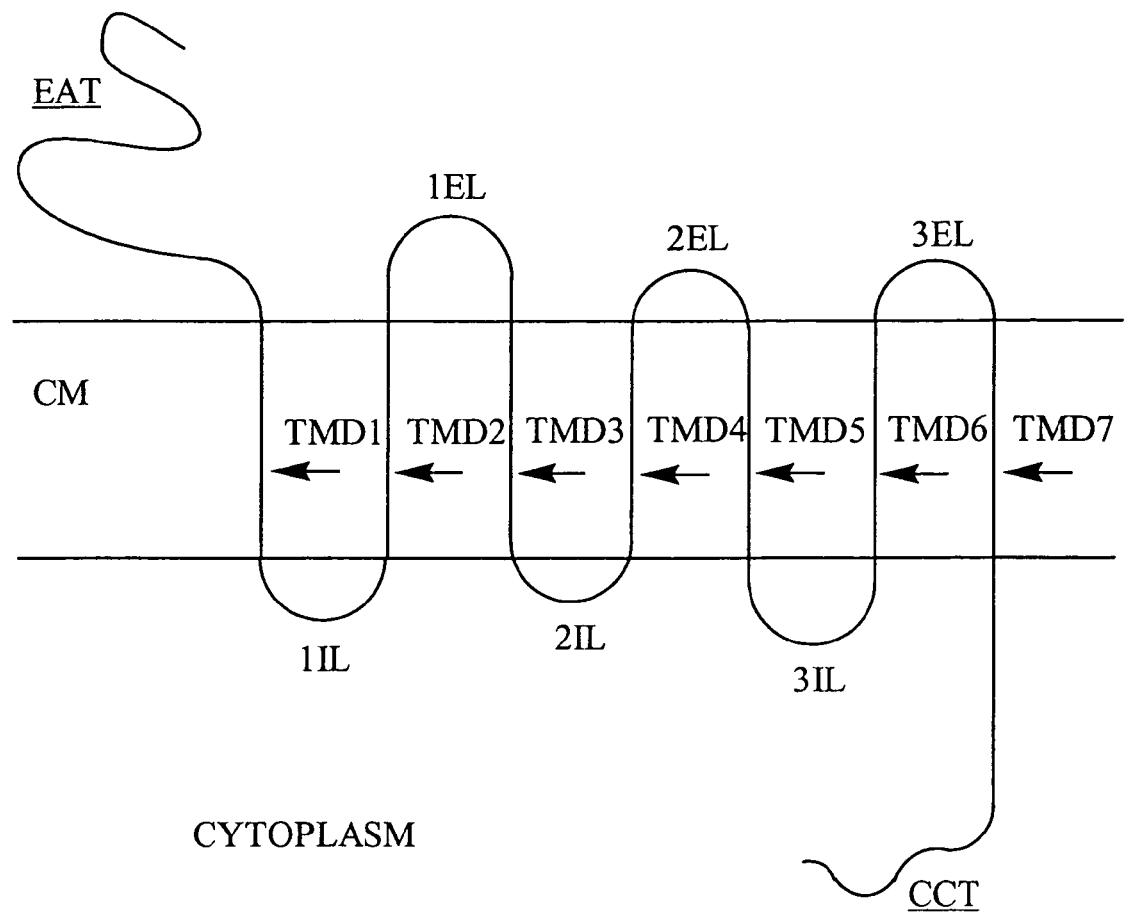
FIG. 1 illustrates the structure of a representative 7TM G protein-coupled receptor. Symbols used are EAT (extracellular amino-terminus), which is encircled by the dotted line; CM (cellular membrane); 1–3IL (first through third intracellular loops); 1–3EL (first through third extracellular loops); TMD 1–7 (first through seventh transmembrane domains); and CCT (cytoplasmic carboxy-terminus).

This invention describes bivalent binding molecules having binding affinity for two or more epitopes of the same 7TM G protein-coupled receptor. In one embodiment the bivalent binding molecules comprise a first binding domain to a first epitope on a first extracellular loop of a 7TM G protein-coupled receptor coupled to a second binding domain to a second epitope on a second extracellular loop of the same 7TM G protein-coupled receptor. In a preferred embodiment at least one binding domain is an aptamer. Also included in this invention are methods for identifying and producing aptamers and bivalent binding molecules to 7TM G protein-coupled receptors. The methods described herein are based on the SELEX method.

1. Definitions

A "bivalent binding molecule" is a compound comprising two or more binding domains having binding affinity to two or more epitopes of the same 7 transmembrane G protein-coupled receptor. In a preferred embodiment at least one of the binding domains is an aptamer. While the majority of the embodiments of bivalent binding molecules disclosed herein are described in terms of having two binding domains, it is to be understood that this invention also includes binding molecules having three binding domains to three different epitopes of the same 7 transmembrane G protein-coupled receptor. Furthermore it is to be understood that these embodiments also include binding molecules having four binding domains to 4 different epitopes on the same 7TM G protein-coupled receptor. The epitopes for which the binding domains are selected may be on the same or different extracellular domains and need not be on adjacent extracellular domains. In a preferred embodiment, all of the binding domains are aptamers. The binding domains may be coupled to each other via a linker. In another embodiment, one of the aptamer binding domains may be replaced by a non-aptamer binding domain that binds to an epitope of the same 7 transmembrane G protein-coupled receptor. The bivalent binding molecules may comprise binding domains which are all agonists, all antagonists or the bivalent molecule may comprise a mixture of agonist and antagonist binding domains.

A "binding domain" is an entity that binds to all or a portion of an extracellular domain of a 7TM G protein-coupled receptor. The binding domain may be a nucleic acid ligand (aptamer), an antibody or antibody fragment, or may be all or a portion of a naturally occurring ligand of the 7TM G protein-coupled receptor.

An "epitope" is a protein domain of a receptor. For the purposes of this invention an epitope may be an entire extracellular portion or a subportion of the extracellular amino terminus or the first through third extracellular loops of a 7TM G protein-coupled receptor as shown in FIG. 1. The epitope may be a synthetic peptide or a recombinantly expressed protein or protein fragment. The 7TM G protein coupled receptor may be expressed in a cell.

A "7 transmembrane G protein-coupled receptor" is a large protein such as that shown in FIG. 1 that transmits a signal from one side of a cell membrane to the other side of the membrane upon binding of an agonist. Members of the superfamily of 7 transmembrane G protein-coupled receptors include those which are listed in Table 1. Examples of biological functions mediated by 7TM G protein-coupled receptors include, but are not limited to, hormone action, neurotransmission, chemotaxis, perception of light, smell and taste, and regulation of blood pressure, heart rate and blood clotting.

A "linker" is a molecular entity that connects two or more molecular entities, and can allow spatial separation of the molecular entities in a manner that preserves the functional properties of one or more of the molecular entities. A linker can also be known as a spacer. Suitable linkers include, but are not limited to, polymers including polyethylene glycol, polypropylene glycol, polyvinyl alcohol, hydrocarbons, polyacrylates and amino-, hydroxy-, thio or carboxy-functionalized silicones; proteins; peptides; polynucleotides; saccharides including monosaccharides, oligosaccharides, cyclodextrins and dextran; other biocompatible moieties; and combinations thereof. A linker may also be a liposome.

An "aptamer" or "nucleic acid ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. For the purposes of this invention, an aptamer is a nucleic acid ligand having specific binding affinity for an epitope on an extracellular membrane of a 7TM G protein-coupled receptor.

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"Target" as used herein means any compound or molecule of interest for which an aptamer is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc., without limitation. In this application, the target is a peptide target comprising all or a portion of an epitope of a 7TM G protein-coupled receptor. A target may also be an enantiomer of a naturally occurring epitope.

An "agonist" is a compound that binds a receptor specific for that compound and elicits a response, i.e., activates the receptor. Thus, the binding of an agonist to its receptor elicits a biological response mediated by the receptor. For the purposes of this invention, the binding of an agonist to a 7TM G protein-coupled receptor is believed to cause a conformational change that enables interaction of the intracellular loops of the receptor with its intracellular G protein.

An "antagonist" is a compound that binds to a receptor such that the compound interferes with the ability of an agonist of that receptor to evoke a response. Thus, the binding of an antagonist to the receptor does not elicit a biological response mediated by the receptor. For the purposes of this invention, binding of an antagonist to a 7 transmembrane G protein-coupled receptor is believed to inhibit signal transduction by causing a conformation that does not allow interaction of the intracellular loops of the receptor with its intracellular G protein.

A "superagonist" is a compound that binds to a receptor in a manner such that it traps a natural ligand in its binding site in the receptor, thereby permanently activating that receptor.

"Lipid constructs", for purposes of this invention, are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others.

"Lipid bilayer vesicles" are closed, fluid-filled microscopic spheres which are formed principally from individual molecules having polar (hydrophilic) and non-polar (lipophilic) portions. The hydrophilic portions may comprise phosphato, glycerylphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable components (including anti-oxidants like alpha-tocopherol) may also be included to improve vesicle stability or confer other desirable characteristics.

"Liposomes" are a subset of lipid bilayer vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into unilamellar vesicles (UV) with the application of a shearing force.

2. The SELEX Method

The SELEX method is described in U.S. patent application Ser. No. 07/536,428, filed Jun. 11, 1990, entitled "Systematic Evolution of Ligands by EXponential Enrichment", now abandoned; U.S. patent application Ser. No. 07/714,131, filed Jun. 10, 1991, entitled "Nucleic Acid Ligands", now U.S. Pat. No. 5,475,096; U.S. patent application Ser. No. 07/931,473, filed Aug. 17, 1992, entitled "Nucleic Acid Ligands", now U.S. Pat. No. 5,270,163, (see also WO 91/19813). These applications, each specifically incorporated herein by reference, are collectively called the SELEX patent applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX patent applications describe and elaborate on this process in great detail. Included are targets that can be used in the process; methods for partitioning nucleic acids within a candidate mixture; and methods for amplifying partitioned nucleic acids to generate an enriched candidate mixture. The SELEX patent applications also describe ligands obtained to a number of target species, including both protein targets where the protein is and is not a nucleic acid binding protein. Each of the above described patent applications which describe modifications of the basic SELEX procedure are specifically incorporated by reference herein in their entirety.

The present invention provides methods for generating bivalent binding molecules and the bivalent binding molecules so produced. A bivalent molecule is defined as a molecule having two or more binding domains having affinity for two or more epitopes of the same 7TM G protein-coupled receptor. In one embodiment, the bivalent binding molecule comprises a first and second binding domain having affinity for a first and second epitope, respectively, of the same 7TM G protein-coupled receptor.

While not wishing to be bound by any theory, it is believed that in embodiments wherein the bivalent binding molecules are agonists, the first and second binding domains bind to their respective epitopes on the extracellular loops of the 7TM G protein-coupled receptor and cause a conformation change to occur in the receptor which enables interaction of the intracellular loops of the receptor with its intracellular G protein.

While not wishing to be bound by any theory, it is believed that in embodiments wherein the bivalent binding molecules are antagonists, the first and second binding domains bind to their respective epitopes on the extracellular loops of the 7TM G protein-coupled receptor and prevent the correct conformational change from occurring in the receptor which ensures that the intracellular loops of the receptor cannot interact with its intracellular G protein.

Further, while not wishing to be bound by any theory, it is believed that in embodiments wherein the bivalent binding molecules are superagonists, the first and second binding domains bind to their respective epitopes on the extracellular loops of the same receptor in a manner which traps a natural agonist in its binding site in the same receptor. As a result the natural agonist "locks" the intracellular loops in a conformation in which they "permanently" interact with the G protein of that receptor, and thus the receptor is in a continual state of activation.

3. Methods of Selecting and Synthesizing Epitopes

In a preferred embodiment, the binding domains of the bivalent compounds described herein are binding domains to epitopes on the extracellular loops of a 7TM G protein-coupled receptor.

In one embodiment, both of the binding domains are aptamers identified by the SELEX process, wherein the targets used to identify the aptamers are epitopes, or protein domains of the 7TM G protein-coupled receptor. In order to identify and define a desired target (i.e., the epitope), the protein corresponding to the receptor (preferably in an extracellular loop) of a 7TM G protein-coupled receptor of interest must be defined. There are a number of methods known in the art for determining the various protein domains. These include hydrophobicity analysis to identify the hydrophobic and hydrophilic segments of the 7TM G protein-coupled receptor and therefore determine those parts of the receptor that comprise the extracellular loops (Heijne, G., *J. Mol. Biol.* 225:487–494 (1992); (Kyte, J., and Doolittle, R. F. (1982) *J. Mol. Biol.*, 157:105–132)). The secondary structure can also be analyzed to identify alpha-helix structures, which make up the hydrophobic regions of the 7TM G protein-coupled receptors. Computer-assisted structural assessment tools that can be used to examine the hydrophobic and hydrophilic segments, the flexibility (Karplus, P. A. and Shultz, G. E. *Naturwissenschaften*, 72:212–213), and secondary structure (Chou, P. Y. and Fasman, G. D. (1976) 47:251–276) of transmembrane domains are also well known in the art (see, for example, Krystek et al. (1985) *Endocrinology* (Baltimore) 117:1125–1131). Correlation of flexibility plots with homology plots and surface profiles may also be helpful in identifying specific regions of protein structure amongst members of the 7TM G protein-coupled receptor.

Once the protein domains of interest are identified, peptides may be prepared consisting of amino acids corresponding to a desired protein domain of the 7TM G protein-coupled receptor of interest. The peptide prepared may be the entire portion of the identified epitope or may be a portion of the epitope. Typically, the peptide comprises between 9 and 100 consecutive amino acids, and preferably between 20 and 50 consecutive amino acids corresponding to the protein domain.

The peptide may be prepared by synthetic methods or may be recombinantly expressed. Methods for peptide synthesis are known in the art and are described in *Solid Phase Peptide Synthesis*, (1984), by Stewart and Young for synthesis by the solid-phase method of Merrifield and in Houben Weyl *Methoden der Otganischen Chemie*, (1974), Vol. 16, parts I & II for solution-phase synthesis. Methods for solution phase synthesis of peptides are also described in U.S. patent application Ser. No. 08/780,517, filed Jan. 8, 1997, entitled "Method for Solution Phase Synthesis of Oligonucleotide and Peptides", now U.S. Pat. No. 5,874,532, the contents of which are incorporated herein by reference. Methods of recombinantly expressing peptides are well known to those of skill in the art.

4. Methods of Generating Bivalent Binding Molecules

A. Generating Bivalent Binding Molecules by the Traditional SELEX Method

In one embodiment, the invention includes bivalent binding molecules to 7TM G protein-coupled receptors comprising a first and second binding domain to a first and second epitope of the same 7TM G protein-coupled receptor, wherein the first and second binding domains are aptamers identified generally according to the method known as the SELEX process. As stated earlier, the SELEX technology is described in detail in the SELEX patent applications which are incorporated herein by reference. In this embodiment, the first and second epitopes are identified, and an aptamer to each epitope is identified by the SELEX method as follows.

An epitope of a 7TM G protein-coupled receptor is identified, and the peptide target for aptamer selection (e.g., all or a portion of the peptide sequence of the epitope) is synthesized by methods known in the art. A candidate mixture of random nucleic acids is prepared and contacted with the peptide target. In general, any protocol which will allow selection of nucleic acids based on their ability to bind specifically to the peptide target can be employed. For example, a filter binding selection, as described in U.S. Pat. No. 5,475,096, may be employed in which a the candidate mixture is incubated with the peptide target under conditions which will allow nucleic acid/peptide target binding pairs to form. The nucleic acid/peptide target binding pairs are isolated by filtering the mixture through a nitrocellulose filter and washing with an appropriate buffer to remove unbound nucleic acids.

In a preferred embodiment, the aptamers are identified by covalently or noncovalently attaching the peptide target to a column (e.g., an affinity column) or other support matrix as described in U.S. Pat. No. 5,475,096. Any standard coupling reagent or procedure may be utilized, depending on the nature of the support. For example, covalent binding may include the formation of disulfide, ester or amide linkages. Noncovalent linkages include antibody-antigen interactions or protein sugar interactions. Other linking chemistries are also available. For example, disulfide-derivatized biotin (Pierce) may be linked to the peptide by coupling through an amine or other functional group. The resulting peptide-biotin complex could then be used with an avidin-derivatized support. Linking chemistries will be selected on the basis of the conditions or reagents necessary for maintaining the structure of the peptide and/or chemical groups on the peptide available for linking to the support matrix. The candidate mixture is added to and incubated with the support to allow nucleic acids having affinity to the peptide to bind to the peptide. The nucleic acid/peptide target binding pairs are separated from unbound nucleic acids by removing unbound nucleic acids from the support, for example, by washing the support with an appropriate buffer which will remove unbound nucleic acids but will not remove the nucleic acid/peptide target binding pairs.

Following the identification of the aptamers for first and second epitopes, the aptamers may be synthesized using standard methods known in the art for synthesizing nucleic acids and then coupled, optionally via a linker. The aptamers may be coupled in any of the following manners:

| Aptamer1 | Aptamer2 |
| --- | --- |
| 3'------------5'-L-5'------------3' | |
| 3'------------5'-L-3'------------5' | |
| 5'------------3'-L-5'------------3' | |
| 5'------------3'-L-3'------------5' | | wherein L represents an optional linker. Methods for coupling aptamers without a linker are known in the art. One method involves solution or solid-phase synthesis of an oligonucleotide sequence corresponding to the sequential combined sequences of both aptamers. The linker may be incorporated using any standard solid phase oligonucleotide synthesis technique known in the art.

After the bivalent molecule is identified, the binding affinity may be measured by methods known in the art. The binding affinity of the bivalent molecule may be tested on the isolated 7TM G protein-coupled receptor or may be tested using a cell line which expresses the protein.

It may be desirable in the process of identifying bivalent binding molecules to remove members of the bivalent molecule library which bind to a second substance. This may be achieved by utilizing a method known as Counter-SELEX, which is described in U.S. Pat. No. 5,580,737, filed Oct. 7, 1993, entitled "High-Affinity Nucleic Acid Ligands That Discriminate Between Theophylline and Caffeine", and in U.S. Pat. No. 5,750,342, filed May 3, 1995, entitled "Nucleic Acid Ligands of Tissue Target". These patents are incorporated herein by reference in their entirety. In one embodiment, a positive selection step is first performed in which the bivalent molecule library is first incubated with cells which express the 7TM G protein-coupled receptor of interest. Those skilled in the field of molecular biology will understand that any of a wide variety of expression systems may be used to provide the recombinant receptor protein. The precise host cell used is not critical to the invention. Cells to which the higher affinity bivalent binding molecules are bound are isolated and the bivalent binding molecules are removed to provide an enriched pool of bivalent binding molecules. In a second, negative selection step, the enriched pool of bivalent binding molecules is then incubated with a second set of cells which are identical to the above cells but which do not express the 7TM G protein-coupled receptor. Those bivalent binding molecules which bind to the second set of cells are discarded, and the remaining bivalent binding molecules are now enriched for bivalent binding molecules with high specificity for the 7TM G protein-coupled receptor.

In a second embodiment, the negative selection step may be performed first with a cell line that does not express the 7TM G protein-coupled receptor of interest, followed by a positive selection step with a cell line that does express the 7TM G protein-coupled receptor.

B. Generating Bivalent Binding Molecules by the Chimeric SELEX Method

In one embodiment, the bivalent binding molecules of the invention are generated by the Chimeric SELEX method. In this embodiment, the binding domains comprise first and second aptamers to first and second epitopes, respectively, on the same 7TM G protein-coupled receptor. The Chimeric SELEX method combines two or more SELEX-evolved nucleic acid ligands and/or nucleic acid libraries (also referred to as parent libraries) into a single chimeric nucleic acid molecule containing the functions of both parent libraries and/or nucleic acid ligands. The chimeric nucleic acid libraries generated may serve as candidate mixtures for further evolution through the SELEX procedure, or they may simply be partitioned for identification of chimeric nucleic acid molecules having the desired characteristics. The Chimeric SELEX method is described in U.S. Pat. No. 5,637,459, filed Aug. 2, 1994, entitled "Systematic Evolution of Ligands by Exponential Enrichment: Chimeric SELEX", the contents of which are incorporated herein by reference.

A "chimeric nucleic acid library" or "chimeric aptamer library" is defined as a collection of molecules, each comprising two aptamers coupled to each other. Each aptamer is derived from a separate parent aptamer library. In the present invention, the parent aptamer libraries are preferably comprised of nucleic acids generated following at least one round of the SELEX process and are enriched in aptamers having binding affinity for two different epitopes of the same 7TM G protein-coupled receptor. The chimeric aptamer libraries of the present invention are also described as bivalent molecule libraries.

In one embodiment of this invention, a method for generating bivalent binding molecules to 7TM G protein-coupled receptors is described, which involves first generating a bivalent molecule library by a method comprising:

(a) generating a first library of aptamers selected through the SELEX procedure for a first epitope of a 7TM G protein-coupled receptor, wherein the aptamers have a 3' fixed sequence, and producing the double-stranded form of the first library of aptamers;

(b) generating a second library of aptamers selected through the SELEX procedure for a second epitope of the same 7TM G protein-coupled receptor, wherein the aptamers have a 5' fixed sequence identical to the 3' fixed sequence of the nucleic acids of the first library, and producing the double-stranded form of the second library of aptamers;

(c) mixing the first and second libraries under conditions which promote interlibrary annealing;

(d) generating bivalent binding molecules by enzymatically extending the recessed 3' ends while copying the 5' extensions of each annealed pair; and (e) amplifying the bivalent binding molecules to generate double-stranded DNA.

In embodiments of the invention where a single-stranded RNA bivalent molecule library is desired, the method further comprises the step:

(f) transcription of the double-stranded DNA to yield a single-stranded RNA bivalent molecule library.

In embodiments of the invention where a single-stranded DNA library is desired, the method further comprises the step:

(f) separating the strands of the double-stranded DNA to yield a single-stranded DNA bivalent molecule library.

The bivalent molecule libraries are then amplified, contacted with the 7TM G protein-coupled receptor, and cycles of selection and amplification are performed to identify a high affinity bivalent molecule to the 7TM G protein-coupled receptor.

In a preferred embodiment, the bivalent molecule library is enriched for higher affinity aptamers for the first and second epitopes prior to selection with the 7TM G protein-coupled receptor by the steps comprising:

(g) contacting the bivalent molecule library with the first epitope, wherein bivalent binding molecules having increased affinity to the first epitope may be partitioned from the bivalent molecule library;

(h) partitioning the bivalent binding molecules having increased affinity to the first epitope from the remainder of the bivalent molecule library;

(i) contacting the bivalent binding molecules having increased affinity to the first epitope with the second epitope, wherein bivalent binding molecules having increased affinity to the first and second epitope may be partitioned from the remainder of the bivalent binding molecules having increased affinity only for the first epitope, thereby generating a bivalent molecule library enriched for bivalent binding molecules having increased affinity for the first and second epitopes. This enriched bivalent molecule library is then screened for members which have high affinity for the 7TM G protein-coupled receptor.

In a preferred embodiment, bivalent binding molecules are selected for the 7TM G protein-coupled receptor which is expressed in a cell. In one embodiment, a negative selection process is employed as described above.

In another embodiment, the bivalent molecule library is generated by placing a monophosphate at the 5'-end of only one of the two parent bivalent molecule libraries and members of the two parent libraries are joined by enzymatic ligation. The 5'-monophosphate may be generated in a number of ways, including by restriction digestion, kinasing, or by priming transcription with a nucleotide monophosphate.

In another embodiment, the first and second libraries are coupled via a linker.

C. Generating Bivalent Binding Molecules by the Blended SELEX Method

In another embodiment, bivalent binding molecules of the invention comprise an aptamer coupled to a non-aptamer binding domain. In this embodiment, the bivalent binding molecules of the invention are generated by the Blended SELEX method. The Blended SELEX method is a method for combining nucleic acids with other functional units for generation of high affinity ligands. Blended SELEX is described in U.S. Pat. No. 5,683,867, filed Apr. 28, 1994, entitled "Systematic Evolution of Ligands by Exponential Enrichment: Blended SELEX", the contents of which are incorporated herein by reference.

In one embodiment of the invention, bivalent binding molecules to a 7TM G protein-coupled receptor are prepared by performing the Blended SELEX method utilizing a candidate mixture of nucleic acids wherein each nucleic acid sequence of the candidate mixture is coupled to a non-aptamer binding domain known to bind to a second epitope of the receptor to form a blended candidate mixture of bivalent binding molecules. The non-aptamer binding domain may be coupled at either the 5' or 3' end of the nucleic acid sequence. Methods of coupling non-aptamer binding domains to nucleic acid sequences are well within the skill of those ordinarily practicing in the art. The blended candidate mixture is contacted with the 7TM G protein-coupled receptor under conditions appropriate for binding of members of the blended candidate mixture to the receptor. Those members of the candidate mixture which bind to the receptor are partitioned from the candidate mixture, amplified, and the bivalent binding molecules having high binding affinity to the receptor are identified.

In another embodiment, bivalent binding molecules to a 7TM G protein-coupled receptor are prepared by performing the traditional SELEX method using an candidate mixture of nucleic acids to identify an aptamer to a first epitope of the 7TM G protein-coupled receptor. The aptamer is then covalently coupled to a non-aptamer binding domain of a second epitope of the same 7TM G protein-coupled receptor to provide a bivalent molecule. Useful non-aptamer binding domains may be all or a portion of a natural ligand to the receptor and include, but are not limited to, antibodies, proteins (including peptides and polypeptides), or their derivatives, including, but limited to, hormones, antigens, synthetic or naturally occurring drugs, and the like; opiates; dopamine; serotonin; catecholamines; thrombin; acetylcholine; prostaglandins; small molecules such as fragrances; pheromones; adenosine; simple sugars such as sucrose, glucose, lactose and galactose; and any other moieties that recognize and have affinity towards an epitope of a 7TM G protein-coupled receptor.

D. Generating Bivalent Binding Molecules by Mirror-Symmetrical Selection

In another embodiment of the method of this invention, a method for identifying bivalent binding molecules to 7TM G protein-coupled receptors is described, wherein the bivalent binding molecules comprise two binding domains, wherein one or both binding domains is an unnatural L-nucleic acid ligand (a mirror image of the natural D-nucleic acid ligand). In this method, one or both of the ligand components are identified by the method described in PCT patent application No. WO 96/34879, entitled "Identification of Enantiomeric Ligands" (Schumacher et al.), and in PCT application No. WO 98/08856, entitled "Mirror-Symmetrical Selection and Evolution of Nucleic Acids" (Fürste, et al.) which describes a method of identifying nucleic acid ligands which are of the opposite chirality from that which occurs in nature (DNA occurs in nature as a D isomer).

In this embodiment, the first step involves synthesizing an enantiomer of a peptide sequence corresponding to the amino acid sequence of the first and/or second epitope(s) of interest (e.g., a D amino acid peptide enantiomer of an L amino acid peptide). The peptide is contacted with a candidate mixture of nucleic acids of natural handedness (i.e., D-DNA or D-RNA) under conditions appropriate for binding. The nucleic acids with high binding affinity for the D amino acid peptide are isolated and their sequences are identified. Nucleic acids of non-natural handedness (i.e., L-DNA or L-RNA), which are mirror images of the high affinity D-DNAs or D-RNAs, are synthesized using enantio-deoxyribose phosphoramidites or enantio-ribose phosphoramidites to yield ligands of non-natural handedness which bind to the natural conformation of the peptide corresponding to the epitope of the receptor. This ligand of non-natural handedness will not be susceptible to nuclease degradation by naturally occurring proteases and nucleases.

In one embodiment, the first and second binding domains are aptamers of non-natural handedness and are identified as described above, and the first and second binding domains are covalently coupled to provide a bivalent ligand. In one embodiment, the binding domains are coupled via a linker.

In another embodiment, the first binding domain is an aptamer of non-natural handedness to a first epitope domain of a receptor identified as described above, and the second binding domain is an aptamer of natural handedness identified by the traditional SELEX method to a second epitope on the same 7TM G protein-coupled receptor. In yet another embodiment, the first binding domain is an aptamer of non-natural handedness to a first epitope of a receptor identified as described above, and the second binding domain is a non-aptamer which binds to a second epitope on the same 7TM G protein-coupled receptor.

5. Linkers

In a preferred embodiment, the first and second binding domains are covalently coupled via a linker. A linker is a molecular entity that connects two or more molecular entities through covalent bonds interactions, and can allow spatial separation of the molecular entities in a manner that preserves the functional properties of one or more of the molecular entities.

In a preferred embodiment, the linker is flexible and of suitable length such that each aptamer of the bivalent molecule is able to bind to its corresponding epitope on the same receptor simultaneously. By flexible it is meant that the linker comprises carbon-carbon sigma bonds having free rotation about their axes.

Suitable linkers include, but are not limited to, polymers including polyethylene glycol, polypropylene glycol, polyvinyl alcohol, hydrocarbons, polyacrylates and amino-, hydroxy-, thio or carboxy-functionalized silicones; proteins; peptides; polynucleotides; saccharides including monosaccharides, oligosaccharides, cyclodextrins and dextran; other biocompatible moieties; and combinations thereof. Such linkers are widely commercially available or obtainable via synthetic organic methods commonly known to those skilled in the art. Methods for coupling such linkers to the ligand domains described herein involve standard organic synthesis and are well known to those of ordinary skill in the art. In addition, the linkers can comprise charged functional groups, such as, for example, ammonium groups of carboxylate groups. The charged functional groups can provide bivalent compounds with increased solubility in aqueous or physiological systems.

As stated above, the linkers should be of sufficient length to allow for the simultaneous binding of both aptamers to their respective epitopes on the same 7TM G protein-coupled receptor. Preferably, the length of the linker is equal or greater to the distance between the two epitopes of the receptor. This distance can be measured, or predicted theoretically, by any method known in the art. For example, molecular modeling can be used to determine the desired length of the linker based on, e.g., the predicted conformation of the receptor. Molecular modeling programs that can be used are commonly known and available in the art.

Linkers may also include lipid bilayer vesicles such as liposomes. U.S. patent application Ser. No. 08/434,465, filed May 4, 1995, entitled "Nucleic Acid Ligand Complexes", now U.S. Pat. No. 6,011,020, describes complexes comprising two or more nucleic acid ligands attached to the surface of the same liposome. U.S. patent application Ser. No. 08/739,109, filed Oct. 25, 1996, entitled "Vascular Endothelial Growth Factor (VEGF) Nucleic Acid Ligand Complexes", now U.S. Pat. No. 5,859,228, describes complexes comprising two or more dialkyl glycerol-derivatized nucleic acid ligands attached to the surface of the same liposome. Each of these applications is incorporated herein by reference in their entirety. In one embodiment of the present invention, the bivalent binding molecules are coupled to a glycerol lipid such as a diacyl glycerol and are associate with the surface of a liposome. The glycerol lipid can associate with the membrane of the liposome in such a way so that bivalent molecule is projecting out of the liposome.

6. Stabilizing Nucleic Acid Ligands

In order to produce aptamers desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

One potential problem encountered in the therapeutic, prophylactic, and in vivo diagnostic use of nucleic acids is that oligonucleotides in their phosphodiester form may be quickly degraded in body fluids by intracellular and extracellular enzymes such as endonucleases and exonucleases before the desired effect is manifested. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, entitled "High Affinity Nucleic Acid Ligands Containing Modified Nucleotides", now abandoned and U.S. patent application Ser. No. 08/434,465, filed May 4, 1995, entitled "Nucleic Acid Ligand Complexes", now U.S. Pat. No. 6,011,020, which are specifically incorporated herein by reference. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the nucleic acid ligands are derived by the SELEX method, the modifications can be pre- or post-SELEX modifications. Pre-SELEX modifications yield nucleic acid ligands with both specificity for their SELEX target and improved in vivo stability. Post-SELEX modifications made to 2'-OH nucleic acid ligands can result in improved in vivo stability without adversely affecting the binding capacity of the nucleic acid ligand. The preferred modifications of the nucleic acid ligands of the subject invention are 5' and 3' phosphorothioate capping and/or 3'—3' inverted phosphodiester linkage at the 3' end. In one preferred embodiment, the preferred modification of the nucleic acid ligand is a 3'—3' inverted phosphodiester linkage at the 3' end. Additional 2' fluoro (2'-F) and/or 2' amino (2'-NH$_2$) and/or 2' O methyl (2'-OMe) modification of some or all of the nucleotides is preferred. Included herein are nucleic acid ligands that were 2'-NH$_2$ modified or 2'-F modified and incorporated into the SELEX process.

Other modifications are known to one of ordinary skill in the art. Such modifications may be made post-SELEX (modification of previously identified unmodified ligands) or by incorporation into the SELEX process. Another example of a post-SELEX modification may be performed as described by Schumacher et al. in PCT application No. WO 96/34879, supra and in Fürste et al. in PCT application No. WO 98/08856. This method involves using an unnatural target molecule (e.g., L-adenosine) to identify a natural D-RNA nucleic acid ligand to that target by the SELEX process, followed by synthesis of the mirror-image of the ligand, i.e., the unnatural L-RNA, which recognizes the natural conformation of the intended target. These unnatural L-RNA nucleic acid ligands are therefore stable in that they are not degraded by nucleases present in human serum, which only recognize natural D-RNA.

7. Uses of Bivalent Binding Molecules

The bivalent binding molecules identified by the methods described herein are useful for both therapeutic and diagnostic purposes. For example, the bivalent binding molecules of the present invention are useful for activating 7TM G protein-coupled receptors specific for that bivalent molecule so as to elicit an appropriate second messenger response, i.e., to initiate a desired physiological response. It is believed that in embodiments wherein the bivalent binding molecules comprise two ligand domains to two different epitopes on the same 7TM G-protein receptor, where each ligand domain is an agonist of its corresponding epitope, that a physiological response will occur with synergistic efficacy greater that that of the individual ligands.

The bivalent binding molecules of the invention are thus useful for treating a disease or condition mediated by a 7TM G protein-coupled receptor. A disease or condition is said to be mediated by a receptor if the symptoms associated with it are caused by or exacerbated by binding of the receptor. It is well within the ability of skilled artisans to determine whether a disease or condition is mediated by a particular receptor. Thus for example, the bivalent binding molecules of the invention may act as antagonists in which they bind to the receptor but do not transmit a signal across the cell membrane in which the receptor resides. The bivalent binding molecules can compete with the natural ligand of the receptor and thereby reduce or prevent interaction between the receptor and the natural ligand. The bivalent binding molecules may also modulate the activity of the receptor by altering the events that occur after the receptor is bound. For example, the bivalent molecule can alter the interaction between the receptor and the G protein with which it naturally interacts, or alter phosphorylation sites present in the intracellular domains of the receptor.

The bivalent binding molecules of the invention may also act as agonists wherein ligand domains of the bivalent molecule bind to their respective epitopes on the same receptor and transmit a signal across the cell membrane.

Therapeutic uses include the treatment or prevention of diseases or medical conditions mediated by 7TM G protein-coupled receptors in human patients, comprising administering an effective amount of a bivalent compound of the present invention. Diseases mediated by 7TM G protein-coupled receptors include inflammatory diseases such as asthma, chronic obstructive pulmonary disease, cystic fibrosis, sinusitis, rhinitis, atherosclerosis, glomerulonephritis, multiple sclerosis, and inflammatory bowel disease. The disease may also be a neurological disease, such as Alzheimer's disease. Therapeutic uses also include the regulation of systolic and/or diastolic blood pressure.

Diagnostic utilization may include both in vivo or in vitro diagnostic applications. The SELEX method generally, and the specific adaptations of the SELEX method taught and claimed herein specifically, are particularly suited for diagnostic applications. The SELEX method identifies nucleic acid ligands that are able to bind targets with high affinity and with surprising specificity. These characteristics are, of course, the desired properties one skilled in the art would seek in a diagnostic ligand.

In embodiments of the invention wherein the bivalent binding molecules of the present invention comprise aptamers, the bivalent binding molecules may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The bivalent binding molecules described herein may specifically be used for identification of 7TM G protein-coupled receptors.

8. Therapeutic Compositions of Bivalent Binding Molecules

Various delivery systems are known in the art and can be used to administer the bivalent compounds of the invention, e.g., aqueous solution, encapsulation in liposomes, microparticles, microcapsules.

Therapeutic compositions of the nucleic acid ligands may be administered parenterally by injection, although other effective administration forms, such as intra-articular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and the nucleic acid ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

9. Effective Dose

The amount of the bivalent compound which will be effective in the treatment of a particular disorder or condition will depend on the nature of the disorder or condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of a bivalent compound of the invention is readily determined by administering graded doses of a bivalent compound of the invention and observing the desired effect.

The following examples are meant to illustrate the method of the invention and are not intended to limit the scope, utility, or applicability of this invention.

EXAMPLE 1

Identification of a Bivalent Binding Molecule to NK1R

The biological actions of substance P, a neurokinin, is mediated by a neurokinin receptor known as NK1R. This receptor is a member of the 7TM G protein-coupled receptor superfamily. Studies have shown that the extracellular domains of the NK1R comprise the ligand binding sites (Fong, T. M. et al. *Journal of Biological Chem.* 267: 25664–25667 (1992)). This example describes the identification of a bivalent molecule to NK1R having affinity for epitopes in extracellular loop 1 and extracellular loop 2.

a) Synthesis of Peptide Target 1 (Epitope 1).

Extracellular loop 1 (ECL1) of NK1R is comprised of the 13 amino acid sequence: N-His-Asn-Glu-Thr-Trp-Tyr-Tyr-Gly-Leu-Phe-Tyr-Cys-Lys-Phe-C (Fong, et al.) (SEQ. ID NO. 1). ECL1 is synthesized by standard peptide synthesis methods known in the art with an additional Cys at the carboxy terminus (ECL1-Cys) to facilitate coupling to a support. ECL1-Cys is covalently coupled (via a disulfide bond) to thiopropyl-activated SEPHAROSE™ 6B matrix through an interaction of the Cys-thiol group of peptides with hydroxypropyl-2-pyridyldisulfide ligands of the matrix as described in U.S. Pat. No. 5,648,214, (Nieuwlandt, et al. supra).

b) Synthesis of Peptide Target 1 (Epitope 2).

Extracellular loop 2 (ECL2) of NK1R is comprised of the 26 amino acid sequence: Thr-Thr-Glu-Thr-Met-Pro-Ser-Arg-Val-Val-Cys-Met-Ile-Glu-Trp-Pro-Glu-His-Pro-Asn-Lys-Ile-Tyr-Glu-Lys-Val (Fong, et al.). ECL2 is synthesized by standard peptide synthesis methods known in the art with an additional Cys at the carboxy terminus (ECL2-Cys) to facilitate coupling to a support. ECL2-Cys is covalently coupled (via a disulfide bond) to thiopropyl-activated Sepharose 6B through an interaction of the Cys-thiol group of peptides with hydroxypropyl-2-pyridyldisulfide ligands of the matrix as described in U.S. Pat. No. 5,648,214, (Nieuwlandt, et al. supra).

c) Random Sequence RNA Pool.

Template DNA for the initial random sequence RNA population is generated from a synthetic random sequence ssDNA pool. The random region is generated by utilizing a mixture of the four unmodified nucleotides (the molar ratios of which are adjusted to yield a 1:1:1:1 ratio of incorporated nucleotides) during oligonucleotide synthesis. The ssDNAs contain 30 nucleotides of contiguous random sequence flanked by defined 5' and 3' ends that permit primer hybridization. Double-stranded DNA (dsDNA) molecules, synthesized initially by Klenow enzyme, and subsequently (following cycles of selection) by Taq DNA polymerase, have a T7 RNA polymerase promoter at the 5' end. In vitro transcription of the dsDNA template yields the initial pool of uniformly [a-$^{32}$P]GTP-labeled random sequence RNAs.

d) Identification of an Aptamer Library 1 to Peptide Target 1.

Uniformly $^{32}$P-labeled RNAs are suspended in an appropriate binding buffer. The suspension is applied to the ECL1-Cys SEPHAROSE™ column, followed by binding buffer wash volumes. Peptide-bound RNAs are then recovered with washes of binding buffer containing dithiothreitol (DTT). DTT reduces the linker disulfide bond resulting in the release of peptide from the matrix. The DTT eluate is extracted with phenol and the RNAs are recovered by ethanol precipitation with yeast tRNA as carrier. Reverse transcription, PCR amplification and T7 RNA polymerase transcription are performed essentially as described in Tuerk and Gold (*Science* 249:505–510 (1990)). Transcription of PCR products yield the RNA pool for the next cycle of selection and amplification. Cycles of selection and amplification are performed as many times as desired to identify high affinity RNA aptamers to epitope 1.

e) Identification of an Aptamer Library 2 to Peptide Target 2.

The protocol described in paragraph d) is followed using the ECL-2-Cys SEPHAROSE™ column to obtain high affinity RNA aptamers to epitope 2.

f) Overlap-extension (OE) Reaction.

Prior to the formation of bivalent binding molecules, double-stranded DNA is generated by PCR from each library in such a way that the 3' fixed sequence of library 1 is identical to the 5' fixed sequence of library 2. Specifically, the 5' primer normally used to amplify library 2 is replaced by a primer that lacks sequences containing the transcriptional promoter. Amplified material from each library is gel purified, and the two libraries are mixed in an OE reaction.

In OE, the DNA is denatured at high temperature and allowed to anneal at 55° C. prior to extension at 72° C. with Taq DNA polymerase. Then two primers, corresponding to the 5' fixed region of library 1 and the 3' fixed region of library 2 are added and PCR performed to generate double stranded DNA to be used as template for further cycles of selection/amplification.

g) Enrichment of the Bivalent Binding Molecule Library

Cycles of the SELEX process are carried out using the bivalent binding molecule library as described in paragraph d) using the peptide 1 affinity column. The bivalent binding molecules which bind to the column are collected and used as the pool in cycles of the SELEX process using the peptide affinity column 2. The bivalent binding molecules that bind to peptide affinity column 2 are collected and screened for their ability to bind NK1R.

h) Selection for NK1R Affinity

The affinity of the enriched bivalent molecule library for NK1R expressed in cells is carried out using the SELEX procedure described in U.S. Pat. No. 5,750,342, filed May 3, 1995, entitled "Nucleic Acid Ligands of Tissue Target", followed by a negative selection using an identical cell line which does not express NK1R. The bivalent binding molecules isolated bind both epitopes 1 and 2 of NK1R.

TABLE 1[a]

Cloned and expressed seven transmembrane receptors

| Receptor | Species | System |
|---|---|---|
| Adenosine | | |
| $A_1$ | rat | A9-L + CHO |
| | human | CHO |
| | canine | CHO |
| $A_{2b}$ | rat | Xenopus oocytes |
| | human | CHO-K1 |
| $A_3$ | sheep | COS-1/CHO K1 |
| $A_3$ | human | CHO |
| Adrenergic | | |
| $\alpha_1$ | hamster | COS-7 |
| $\alpha_1$ | bovine | COS-7 |
| $\alpha_2$ | human | COS-7 |
| | | CHO |
| | mouse | COS-7 |
| | | Xenopus oocytes |
| | fish | COS-7 |
| $\alpha_{2C}$ | mouse | |
| | rat | CHO/COS-7 |
| $\alpha_{2A}$ | human | COS-7 |
| | human | COS 1 |
| $\alpha_{2B}, \alpha_{2C}, \alpha_{2D}$ | rat | NIH 3T3 |
| $\alpha_{2b}$ | rat | COS |
| | human | Ltk cells |
| $\alpha_{2D}$ | rat | COS 1 |
| $\alpha_{2A}$ | human | Xenopus oocytes |
| | porcine | COS-M6 |
| $\alpha_{2B}$ | rat | COS |
| $\alpha_{1D}$ | human | SK-N-MC |
| $\beta_1$ | rat | L cells |
| | human | Xenopus oocytes |
| | mouse | COS-7/L-cells sf9 |
| $\beta_1/\beta_2$ | human | CHO |
| $\beta_2$ | mouse | Y-1 |
| | human | Escherichia coli |
| $\beta_3$ | mouse | CHO |
| | rat | CHO |
| | human | CHO cells |
| Calcium | bovine | Xenopus oocytes |
| Dopamine | | |
| $D_1$ | human | |
| | rat | COS-7 |
| | human | COS-7 |
| | rhesus | C6 cells |
| $D_{1B}$ | rat | COS-7 |
| $D_2$ | human | COS-7 |
| | mouse | COS-7 |
| | rat | COS-7 |
| | | CHO-6, DUK 25 |
| | rat | mouse fibroblasts |

TABLE 1[a]-continued

Cloned and expressed seven transmembrane receptors

| Receptor | Species | System |
|---|---|---|
| $D_2/D_3$ | human | CHO |
| $D_2/D_3$ | rat | LZR1, Ltk 59 |
| $D_3$ | rat | CHO |
| $D_4$ | human | COS-7 |
| $D_5$ | human | COS-7 |
| Histamine | | |
| $H_1$ | bovine | COS-7 |
| $H_2$ | rat | CHO |
| | canine | L-cells |
| | human | Colo-320 |
| Muscarininc | | |
| muscarininc | porcine | Xenopus oocytes |
| muscarininc | porcine | CHO |
| muscarininc | drosoph. | Y-1 cells |
| m1 | mouse | Y-1, L-cells |
| | human | CHO-K1 |
| m1, m2 | human | HEK |
| m2 | human | CHO-K1 |
| m3 | human | CHO-K1 |
| | | CHO |
| m4 | chicken | Y1/CHO |
| | human | CHO-K1 |
| m5 | human/rat | COS-7 |
| | | CHO-K1 |
| Opioid | | |
| κ | mouse | PC-12 |
| | | COS-1 |
| | human | COS-1 |
| | rat | COS-7/Xenopus oocytes |
| | | COS-7 |
| δ | mouse | CHO-DGH4 |
| | human | CHO |
| | | COS |
| μ | rat | COS-7 |
| | | COS-7 |
| | | COS-7 |
| δ | human | COS-7 |
| | mouse | COS-1 |
| μ | human | COS-7 |
| Peptides | | |
| Angiotensisn type 2 | human | COS-7 |
| | mouse | COS-7 |
| | rat | COS-7 |
| Bradykinin | | |
| $B_2$ | rat | Xenopus oocytes |
| | human | COS-7 |
| Calcitonin | | |
| | human | |
| | rat | |
| | pig | COS |
| Cholecystokin | | |
| A | human | COS |
| | rat | Xenopus oocytes |
| B | human | COS-7 |
| Choriogonadotropin | porcine | COS-7 |
| Corticotropin releasing factor | rat | COS-7 |
| $Endothelin_B$ | human | COS-7 |
| Gastrin | canine | COS-7 |
| Glucagon | rat | BHK |
| Gonadotropin releasing hormone | human | COS-7 |
| Growth hormone releasing hormone | rat | HEK 293 |
| Lutropin/luteinizing hormone | rat | HEK 292 |
| | mouse | L cells |
| Neuropeptide Y | rat | 293 |
| $Neurotensin_A$ | human | Baculovirus |
| Parathyroid hormone | opossum | COS-7 |
| | rat | COS |
| Secretin | rat | COS |
| | human | HEK 293 |
| Somatostatin | mouse/human | CHO |

TABLE 1ª-continued

Cloned and expressed seven transmembrane receptors

| Receptor | Species | System |
|---|---|---|
| R1 | rat | COS-7 |
|  | human | CHO |
| R2 | mouse | CHO |
| R3 | rat | COS |
|  | human | COS-1 |
|  | mouse | CHO |
| R4 | human | COS-7 |
|  | human | COS-1 |
|  | mouse | COS-1DM |
| R4, R5 | human | CHO-K1/COS-1 |
| R5 | human | CHO-K1 |
|  | human | COS-7 |
| Substance P | murine | Xenopus oocytes |
|  | rat | COS |
|  | human | COS-7 |
| TSH Thyrotropin | human | COS-7 |
|  | canine | COS |
|  | rat | CHO-K1 |
| VIP | rat | COP |
|  | human | COS-6 |
| 5-HT |  |  |
| 1 | rat | HEK 293 |
| 1A | rat | Ltk |
|  | human | monkey kidney NIH 3T3 |

TABLE 1ª-continued

Cloned and expressed seven transmembrane receptors

| Receptor | Species | System |
|---|---|---|
| 1B | rat | Y-1 |
|  | human | sf9 |
|  |  | HeLa |
|  | mouse | NIH 3T3 |
| 1C | human | Xenopus oocytes |
|  | mouse | Xenopus oocytes |
| 1D | canine | COS-7 |
|  | human | CHO-K1 |
| 1E | human | murine L cells |
| 2 | rat | (mammalian) |
| 2B | human | AV12-664 |
| 3 | mouse | COS-1/Xenopus oocytes |
| 5A, 5B | mouse | COS-7 |
| 5A | human | Cos M6 |
| (S12) | human | Ltk |
| 7 | rat | COS-7, HEK 293 |
| GP2-7 | guinea pig | CHO-K1 |

ªKenakin, T. Pharmacological Reviews, 48: 413–463 (1996).

---

The invention claim is:

1. A bivalent binding molecule to a 7 transmembrane G protein-coupled receptor, wherein said bivalent binding molecule comprises an aptamer to a first epitope coupled to a non-aptamer binding domain which binds to a second epitope of the same receptor, wherein the bivalent binding molecule is identified according to a method comprising:
    a) preparing a blended candidate mixture of bivalent binding molecules comprising a candidate mixture of nucleic acid sequences coupled to a non-aptamer binding domain which binds to said second epitope of the receptor;
    b) contacting said 7 transmembrane G protein-coupled receptor with said blended candidate mixture of bivalent binding molecules, wherein bivalent binding molecules having an increased affinity to the 7 transmembrane G protein-coupled receptor relative to the blended candidate mixture may be partitioned from the remainder of the candidate mixture;
    c) partitioning the increased affinity bivalent binding molecules from the remainder of the blended candidate mixture; and
    d) amplifying the increased affinity bivalent binding molecules to yield an enriched mixture of bivalent binding molecules, whereby bivalent binding molecules to a 7 transmembrane G protein-coupled receptor may be identified.

2. The bivalent binding molecule of claim 1 wherein the binding domains are coupled to each other via a linker.

3. The bivalent binding molecule of claim 2 wherein said linker is selected from the group consisting of polyethylene glycol, polypropylene glycol, polyvinyl alcohol, hydrocarbons, polyacrylates and amino-, hydroxy-, thio or carboxy-functionalized silicones, proteins, peptides, polynucleotides, monosaccharides, oligosaccharides, cyclodextrins, dextran and liposomes.

4. The bivalent binding molecule of claim 1 wherein the aptamer binding domain is coupled at the 3' end to another binding domain.

5. The bivalent binding molecule of claim 1, wherein said 3 transmembrane G protein-coupled receptor is selected from the group consisting of adenosine, adrenergic, calcium, dopamine, histamine, muscarinic, opioid, and peptide receptors.

* * * * *

UNITED STATES PATENT AND TRADEMARK OFFICE
CERTIFICATE OF CORRECTION

PATENT NO. : 7,087,735 B2
APPLICATION NO. : 10/729667
DATED : August 8, 2006
INVENTOR(S) : Larry Gold It is certified that error appears in the above-identified patent and that said Letters Patent is hereby corrected as shown below:

Column 28, line 17 replace --
"3 transmembrane G protein-coupled receptor is selected"
with
-- 7 transmembrane G protein-coupled receptor is selected --.

Signed and Sealed this

Twenty-fourth Day of October, 2006

JON W. DUDAS
*Director of the United States Patent and Trademark Office*